United States Patent
Fisher et al.

(10) Patent No.: US 12,419,531 B2
(45) Date of Patent: Sep. 23, 2025

(54) IMPLEMENTING A PERIODIC DEOXYHEMOGLOBIN SIGNAL

(71) Applicant: THORNHILL SCIENTIFIC INC., North York (CA)

(72) Inventors: Joseph Arnold Fisher, Thornhill (CA); James Duffin, Toronto (CA); Julien Poublanc, North York (CA); Olivia Sobczyk, Etobicoke (CA); David J. Mikulis, Oakville (CA); Ece Su Sayin, Windsor (CA)

(73) Assignee: THORNHILL SCIENTIFIC INC., North York (CA)

( * ) Notice: Subject to any disclaimer, the term of this patent is extended or adjusted under 35 U.S.C. 154(b) by 59 days.

(21) Appl. No.: 18/579,311

(22) PCT Filed: Jul. 18, 2022

(86) PCT No.: PCT/IB2022/056604
§ 371 (c)(1),
(2) Date: Jan. 12, 2024

(87) PCT Pub. No.: WO2023/286040
PCT Pub. Date: Jan. 19, 2023

(65) Prior Publication Data
US 2024/0335128 A1  Oct. 10, 2024

Related U.S. Application Data

(60) Provisional application No. 63/222,858, filed on Jul. 16, 2021.

(51) Int. Cl.
*A61B 5/026* (2006.01)
*A61B 5/00* (2006.01)
(Continued)

(52) U.S. Cl.
CPC .......... *A61B 5/0263* (2013.01); *A61B 5/0042* (2013.01); *A61B 5/055* (2013.01);
(Continued)

(58) Field of Classification Search
CPC ..... A61B 5/0263; A61B 5/0042; A61B 5/055; A61B 5/7257; A61B 2576/026; A61B 5/145; A61B 5/0205; G01R 33/5601
See application file for complete search history.

(56) References Cited

U.S. PATENT DOCUMENTS

2016/0220115 A1   8/2016   Fisher et al.

FOREIGN PATENT DOCUMENTS

| CA | 2758393 A1 | 10/2009 | |
|---|---|---|---|
| CA | 2845308 A1 | 11/2012 | |
| WO | WO-2021137196 A1 * | 7/2021 | ........... A61B 5/0044 |

OTHER PUBLICATIONS

Han 2010 MS thesis University of Toronto; 105 pages (Year: 2010).*

* cited by examiner

*Primary Examiner* — Keith M Raymond
*Assistant Examiner* — Patrick M Mehl
(74) *Attorney, Agent, or Firm* — Perry + Currier Inc.

(57) ABSTRACT

A method of implementing changes in deoxyhemoglobin concentration, the method comprising: targeting a sequence of partial pressures of oxygen in arterial blood (PaCh) values in a subject using a sequential gas delivery device in a periodic input pattern; measuring a blood-oxygen level dependent (BOLD) signal in a voxel of the subject's brain using a magnetic resonance imaging device while targeting the sequence of values; comparing the pattern to the signal;
(Continued)

and determining a vascular tissue characteristic (vessel type, vessel orientation, or pathological condition) for the voxel based on the comparison.

12 Claims, 6 Drawing Sheets

(51) Int. Cl.
    *A61B 5/055*     (2006.01)
    *G01R 33/56*     (2006.01)

(52) U.S. Cl.
    CPC ........ *A61B 5/7257* (2013.01); *G01R 33/5601* (2013.01); *A61B 2576/026* (2013.01)

IMPLEMENTING A PERIODIC DEOXYHEMOGLOBIN SIGNAL

CROSS-REFERENCE TO RELATED APPLICATION(S)

This application claims the benefit of U.S. provisional application entitled FREQUENCY MODULATION OF DEOXYHEMOGLOBIN CONCENTRATION AS MEASURED BY BOLD SIGNAL, having Ser. No. 63/222,858, filed Jul. 16, 2021 and incorporated by reference herein.

FIELD

The present specification is directed to perfusion magnetic resonance imaging (MRI), and specifically dynamic susceptibility contrast MRI with deoxyhemoglobin as the contrast agent.

BACKGROUND

Due to its paramagnetic properties, concentrations of deoxyhemoglobin can be measured in the tissues using blood oxygen level dependent (BOLD) magnetic resonance imaging (MRI). When blood flow in a tissue increases beyond its metabolic requirements, the [dOHb] is reduced by virtue of being diluted by the "excess" oxyhemoglobin. Thus, the changes in BOLD signal are surrogate markers of the degree of blood flow.

BOLD signals in the brain have been known to fluctuate in rapid complex patterns called the default mode network (DMN). This network is identified by collecting abundant BOLD signal data while the person is at rest over a period and then using complex analysis such as cross correlation, grouping the closest matching voxels into a DMN map. A pattern that is useful for matching has an ultra-low frequency modulation (ULFM). The source of this modulation is unknown, however the oscillations are thought to reflect, to some extent, vascular functions.

When the DMN is known, asymmetries in arrival time, or "time to peak" can be used to identify unilateral vascular pathologies such as upstream stenosis, ischemia, chronic ischemia, Parkinson's Disease, Alzheimer's, and aging.

SUMMARY

An aspect of the specification a method of determining a tissue characteristic by implementing a periodic deoxyhemoglobin signal in a subject. A sequential gas delivery device implements a deoxyhemoglobin signal in a periodic pattern (such as a sinusoidal pattern) by targeting a sequence of partial pressures of oxygen in arterial blood (PaO$_2$) in a subject. While targeting the sequence of PaO$_2$, a magnetic resonance imaging (MRI) device measures a magnetic signal in a voxel of the subject's brain. Then, the periodic pattern of the input signal is compared to the magnetic signal measured by the MRI device. Based on this comparison, a tissue characteristic for the voxel is determined.

These together with other aspects and advantages which will be subsequently apparent, reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

Embodiments are described with reference to the following figures.

DETAILED DESCRIPTION

List of Abbreviations

"AIF" herein refers to arterial input function.
"ASL" herein refers to arterial spin labelling.
"BOLD" herein refers to Blood Oxygen Level Dependent.
"CBF" herein refers to "cerebral blood flow".
"CMRO$_2$" herein refers to the metabolic rate of oxygen.
[dOHb] herein refers to the concentration of deoxyhemoglobin in a subject's blood.
"FRC" herein refers to functional residual capacity.
"OEF" herein refers to oxygen extraction fraction.
"MTT" herein refers to mean transit time.
"PCO$_2$" herein refers to the partial pressure of carbon dioxide.
"PO$_2$" herein refers to the partial pressure of oxygen.
"P$_a$O$_2$" herein refers to the arterial partial pressure of oxygen.
"P$_a$CO$_2$" herein refers to the arterial partial pressure of carbon dioxide.
"PET" herein refers to positron emission tomography.
"P$_{ET}$O$_2$" herein refers to the end tidal partial pressure of oxygen.
"P$_{ET}$CO$_2$" herein refers to the end tidal partial pressure of carbon dioxide.
"ROI" herein refers to a region of interest.
"SGD" herein refers to sequential gas delivery and may refer either to a device or a method.
"S$_a$O$_2$" herein refers to the arterial blood-oxygen saturation.
"ULFM" herein refers to ultra-low frequency modulation.
"VT" herein refers to tidal volume.

Using the DMN to identify pathologies has several limitations. Firstly, the DMN is a highly complex pattern, which makes complicates the analysis and certainty in the results. Furthermore, little is known about vasculature, vascular physiology, and brain function in voxels that do not participate in the DMN. Even for voxels in the DMN, little is known other than arrival delay and synchrony.

The present disclosure provides a method of implementing a periodic [dOHb] signal in a subject and identifying a tissue characteristic in a selected voxel based on the [dOhb] signal.

Figure 1:
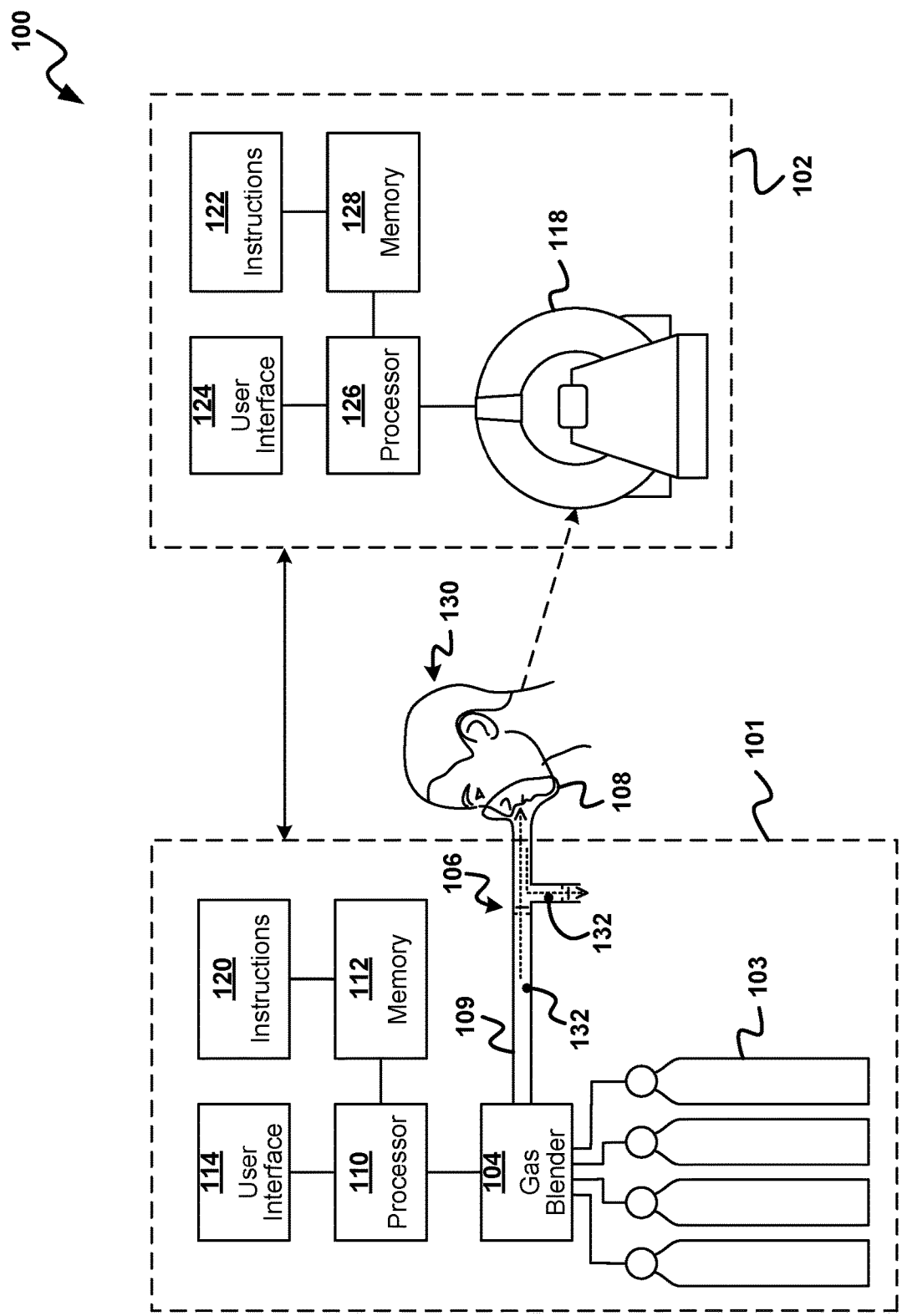
FIG. 1 is a block diagram of a system for implementing a periodic deoxyhemoglobin signal.

FIG. 1 shows a system 100 for identifying a tissue characteristic in a subject. The system 100 includes a device 101 to provide sequential gas delivery to a subject 130 and target a P$_a$O$_2$ while maintaining normocapnia. The system 100 further includes a magnetic resonance imaging (MRI) system 102. The device 101 includes gas supplies 103, a gas blender 104, a mask 108, a processor 110, memory 112, and a user interface device 114. The device 101 may be configured to control end-tidal partial pressure of CO$_2$ (P$_{ET}$CO$_2$) and end-tidal partial pressure of O$_2$ (P$_{ET}$O$_2$) by generating predictions of gas flows to actuate target end-tidal values. The device 101 may be an RespirAct™ device (Thornhill Medical™: Toronto, Canada) specifically configured to implement the techniques discussed herein. For further information regarding sequential gas delivery, U.S. Pat. No. 8,844,528, US Publication No. 2018/0043117, and U.S. Pat. No. 10,850,052, which are incorporated herein by reference, may be consulted.

The gas supplies 103 may provide carbon dioxide, oxygen, nitrogen, and air, for example, at controllable rates, as defined by the processor 110. A non-limiting example of the gas mixtures provided in the gas supplies 103 is:
   a. Gas A: 10% $O_2$, 90% $N_2$;
   b. Gas B: 10% $O_2$, 90% $CO_2$;
   c. Gas C: 100% $O_2$; and
   d. Calibration gas: 10% $O_2$, 9% $CO_2$, 81% $N_2$.

The gas blender 104 is connected to the gas supplies 103, receives gases from the gas supplies 103, and blends received gases as controlled by the processor 110 to obtain a gas mixture, such as a first gas (G1) and a second gas (G2) for sequential gas delivery.

The second gas (G2) is a neutral gas in the sense that it has about the same $PCO_2$ as the gas exhaled by the subject 130, which includes about 4% to 5% carbon dioxide. In some examples, the second gas (G2) may include gas actually exhaled by the subject 130. The first gas (G1) has a composition of oxygen that is equal to the target $P_{ET}O_2$ and preferably no significant amount of carbon dioxide. For example, the first gas (G1) may be air (which typically has about 0.04% carbon dioxide), may consist of 21% oxygen and 79% nitrogen, or may be a gas of similar composition, preferably without any appreciable $CO_2$.

The processor 110 may control the gas blender 104, such as by electronic valves, to deliver the gas mixture in a controlled manner.

The mask 108 is connected to the gas blender 104 and delivers gas to the subject 130. The mask 108 may be sealed to the subject's face to ensure that the subject only inhales gas provided by the gas blender 104 to the mask 108. In some examples, the mask is sealed to the subject's face with skin tape such as Tegaderm™ (3M™, Saint Paul, Minnesota). A valve arrangement 106 may be provided to the device 101 to limit the subject's inhalation to gas provided by the gas blender 104 and limit exhalation to the room. In the example shown, the valve arrangement 106 includes an inspiratory one-way valve from the gas blender 104 to the mask 108, a branch between the inspiratory one-way valve and the mask 108, and an expiratory one-way valve at the branch. Hence, the subject 130 inhales gas from the gas blender 104 and exhales gas to the room.

The subject may breathe spontaneously or be mechanically ventilated.

The gas supplies 103, gas blender 104, and mask 108 may be physically connectable by a conduit 109, such as tubing, to convey gas. Any number of sensors 132 may be positioned at the gas blender 104, mask 108, and/or conduits 109 to sense gas flow rate, pressure, temperature, and/or similar properties and provide this information to the processor 110. Gas properties may be sensed at any suitable location, so as to measure the properties of gas inhaled and/or exhaled by the subject 130.

The processor 110 may include a central processing unit (CPU), a microcontroller, a microprocessor, a processing core, a field-programmable gate array (FPGA), an application-specific integrated circuit (ASIC), or a similar device capable of executing instructions. The processor may be connected to and cooperate with the memory 112 that stores instructions and data.

The memory 112 includes a non-transitory machine-readable medium, such as an electronic, magnetic, optical, or other physical storage device that encodes the instructions. The medium may include, for example, random access memory (RAM), read-only memory (ROM), electrically erasable programmable read-only memory (EEPROM), flash memory, a storage drive, an optical device, or similar.

The user interface device 114 may include a display device, touchscreen, keyboard, buttons, the like, or a combination thereof to allow for operator input and/or output.

Instructions 120 may be provided to carry out the functionality and methods described herein. The instructions 120 may be directly executed, such as a binary file, and/or may include interpretable code, bytecode, source code, or similar instructions that may undergo additional processing to be executed. The instructions 120 may be stored in the memory 112.

System 100 further includes an MRI system 102 for conducting magnetic resonance imaging on the subject 130. A suitable MRI system may include an imaging device such as a 3T MRI system (Signa HDxt-GE Healthcare, Milwaukee). The MRI system 102 may further include a processor 126, memory 128, and a user interface 124. Any description of the processor 126 may apply to the processor 110 and vice versa. Likewise, any description of memory 128 may apply to memory 112 and vice versa. Similarly, any description of instructions 112 may apply to instructions 120 and vice versa. Also, any description of user interface 124 may apply to user interface 114, and vice versa. In some implementations, the MRI system 102 and the device 101 share one or more of a memory, processer, user interface, and instructions, however, in the present disclosure, the MRI system 102 and the device 101 will be described as having respective processors, user interfaces, memories, and instructions. The processor 110 of the device 101 transmits data to the processor 126 of the MRI system 102. The system 100 may be configured to synchronize MRI imaging obtained by the MRI system 102 with measurements obtained by the device 101.

The processor 126 may retrieve operating instructions 122 from the memory or may receive operating instructions 122 from the user interface 124. The operating instructions 122 may include image acquisition parameters. The parameters may include an interleaved echo-planar acquisition consisting of a number of contiguous slices, a defined isotropic resolution, a diameter for the field of view, a repetition time, and an echo time. In one implementation, the number of contiguous slices is 27, the isotropic resolution is 3 mm, the field of view is 19.6 cm, the echo time is 30 ms, and the repetition time (TR) is 2000 ms, however a range of values will be apparent to a person of ordinary skill in the art. The operating instructions 122 may also include parameters for a high-resolution T1-weighted SPGR (Spoiled Gradient Recalled) sequence for co-registering the BOLD images and localizing the arterial and venous components. The SPGR parameters may include a number of slices, a dimension for the partitions, an in-plane voxel size, a diameter for the field of view, an echo time, and a repetition time. In one implementation, the number of slices is 176 m, the partitions are 1 mm thick, the in-plane voxel size is 0.85 by 0.85 mm, the field of view is 22 cm, the echo time is 3.06 ms, and the repetition time (TR) is 7.88 ms.

The processor 126 may be configured to analyze the images using image analysis software such as Matlab 2015a and AFNI or other processes generally known in the art. As part of the analysis, the processor 126 may be configured to perform slice time correction for alignment to the same temporal origin and volume spatial re-registration to correct for head motion during acquisition. The processor 126 may be further configured to perform standard polynomial detrending. In one implementation, the processor 126 is configured to detrend using AFNI software 3dDeconvolve to obtain detrended data.

Figure 2:
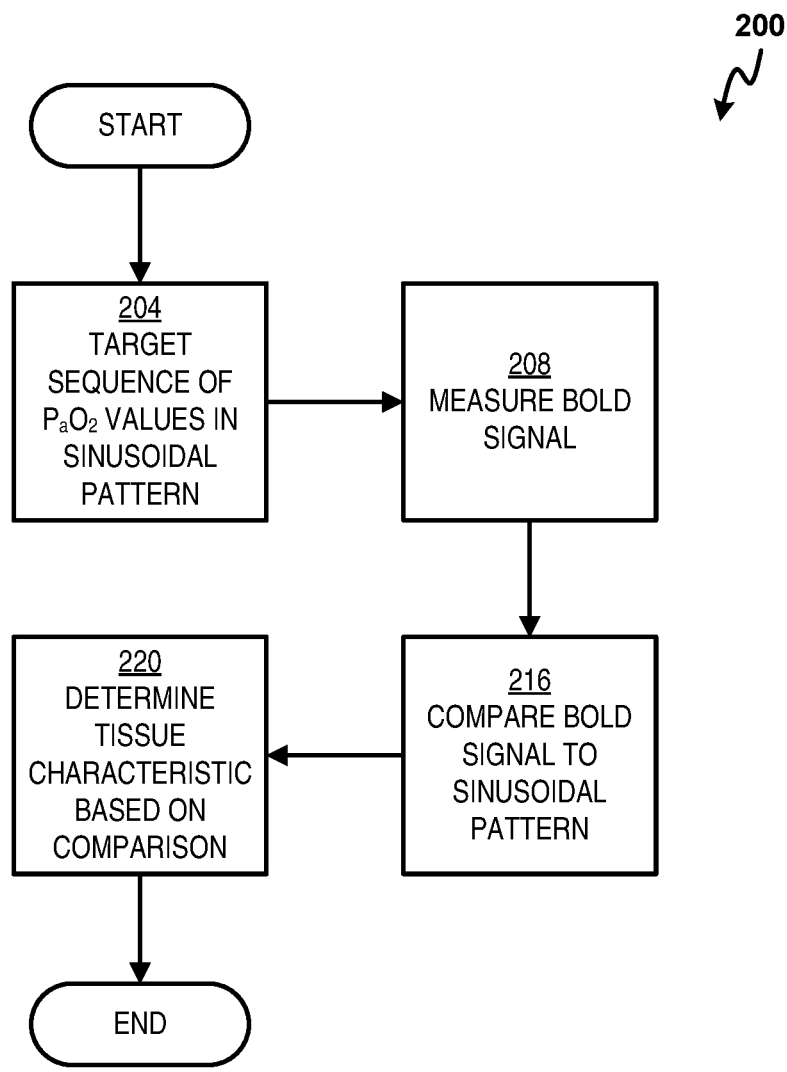
FIG. 2 is a flowchart of a method for implementing a periodic deoxyhemoglobin signal.

FIG. 2 shows an example method 200 of implementing a periodic deoxyhemoglobin signal in a subject. The method 200 may be implemented by instructions 120 stored on memory 112 and implemented by processor 110 and/or instructions 122 stored in memory 128 and implemented by processor 126.

At block 204, the instructions 120 control the device 101 to alternately target a sequence of $P_aO_2$ values in a periodic pattern. The periodic pattern has a $PaO_2$ value corresponding to a trough value and a $PaO_2$ value corresponding to a peak value; the trough value representing a minimum value in the periodic pattern and the peak value representing a maximum value in the periodic pattern. Examples of suitable periodic patterns include a sinusoidal pattern, an alternating ramp sequence, an alternating square wave sequence, a saw-tooth pattern, the like, or any combination thereof. The periodic pattern functions as an input signal. In non-limiting examples described herein, the device 101 targets a sinusoidal input pattern.

The sinusoidal input pattern may have a set amplitude defined as the difference between the peak $P_aO_2$ value and trough $P_aO_2$ value. The difference between the peak $P_aO_2$ value and the trough $P_aO_2$ value should be significant enough to induce a measurable change in [dOHb] in the subject. The amplitude of the signal will be proportional to the change in hemoglobin saturation. Therefore, increasing the amplitude of the [dOHb] change will decrease the signal to noise ratio (SNR). In some examples, the trough and peak $P_aO2$ values are selected to cause an amplitude of about 1 to 50% in the [dOHb].

The sinusoidal input pattern may have a predetermined frequency. In some examples, the predetermined frequency is selected to contrast with naturally-occurring frequencies such as the default mode network (DMN). Since the DMN is best modelled as an ultra-low frequency modulation (ULFM) which as a frequency of about 0.1 hertz, the predetermined frequency may between 0.1 hertz and 0.001 hertz. In a non-limiting example, the device 101 implements a frequency of 0.017 hertz.

In some examples, the device 101 implements the predetermined frequency for a first duration of time and then implements another frequency for a second duration of time. In further examples, the device 101 implements the predetermined frequency for a first duration of time and then implements a non-periodic stimulus such as a single step change, multiple steps, or a ramp sequence in $P_aO_2$.

As the device 101 is targeting the sequence of $P_aO_2$ values in the sinusoidal input pattern, the device 101 may further vary the $PCO_2$. Sequential gas delivery devices such as the RespirAct™ are capable of controlling $PCO_2$ independently from $PO_2$. The device 101 may maintain $PCO_2$ at a constant level or the device 101 may fluctuate the $PCO_2$ in a periodic pattern. In examples where the $PCO_2$ is maintained, the device 101 may maintain the $PCO_2$ between 15 mmHg and 90 mmHg. In examples where the $PCO_2$ fluctuates, the device 101 may control the $PCO_2$ in the same pattern as the $PO_2$ or a contrasting pattern. Examples of a periodic pattern include: a sinusoidal pattern, a ramp sequence, a step sequence, a saw-tooth pattern, the like, or any combination thereof. $PCO_2$ is known to increase cerebral blood flow in tissues, and therefore may increase the amplitude of the magnetic signal obtained later at block 208.

At block 208, the instructions 120 control the device 102 to measure a magnetic signal in a voxel of the subject's brain. In one example, the device 102 measures a T2* dependent signal, also called the Blood Oxygen-Level Dependent (BOLD) signal. Block 208 is performed concurrently with block 204 so that the measured signal is reflective of the sinusoidal input pattern induced at block 204. The measured signal may also be characterized as a sinusoidal signal having an amplitude, periodic, and frequency. The measured signal indicates that the [dOHb] in the subject is changing in a sinusoidal fashion as the $P_aO_2$ changes.

At block 216, the instructions 122 control the processor 126 to compare the sinusoidal output pattern of the magnetic signal measured at block 208 with the sinusoidal input signal pattern implemented at block 204 and measured as a signal in the main arteries such as the carotid artery and middle cerebral artery.

As part of block 216, the processor may compute one or more characteristics of the sinusoidal input pattern implemented at block 204. The characteristic of the sinusoidal input pattern may include the amplitude, frequency, and period. In some examples, the processor 126 computes the amplitude, frequency, and period of the sinusoidal input pattern. Before determining the characteristic of the sinusoidal input pattern, the sinusoidal input pattern may be converted from end tidal partial pressure of oxygen ($P_{ET}O_2$) to $S_aO_2$ using the Hill equation shown below as Equation 1.

$$S_aO_2 = 100\frac{K(P_{ET}O_2)^n}{1 + K(P_{ET}O_2)^n} \qquad \text{Equation 1}$$

In Equation 1, the dissociation constant (K) and the Hill coefficient (n) are determined using methods described in Balaban et al., 2013. In one implementation of Equation 1, n=−4.4921 pH, K=5.10$^{-142}$ pH$^{157.31}$, and pH=7.4. [dOHb]=[dOHb]×(1−SaO$_2$).

The instructions 122 may similarly control the processor 126 to compute a characteristic of the magnetic signal measured at block 208. The characteristic computed at block 212 may include the amplitude, frequency, period, and phase lag of the sinusoidal output pattern of the magnetic signal, or a combination thereof. In some examples, the processor 126 computes the amplitude, frequency, period, and phase lag of the magnetic signal.

As part of block 216, the instructions 122 may control the processor 126 to conduct a Fourier Transform to identify the dominant frequency of the magnetic signal in voxels over major arteries such as the carotid artery or middle cerebral artery. In these examples, the characteristic of the magnetic signal is based on the dominant frequency of the magnetic signal as measured from major arteries such as carotid artery and middle cerebral artery. Phase lag from these arterial inputs indicates dispersion in the tissue Amplitude of the magnetic signal may be computed as the difference between the maximum magnetic signal and the minimum magnetic signal measured in the voxel. Period may be computed based on the time between peaks. Frequency may be computed as the inverse of the period.

Phase lag may be computed based on a comparison of the frequency of the magnetic signal to the frequency of the arterial input frequency (AIF). Phase lag represents the blood transit time in a vessel and is used interchangeably with arrival delay and/or dispersion. The AIF may be determined based on the BOLD signal over an artery, such as the middle cerebral artery or the choroid plexus in the ventricles.

As part of block 216, the processor 126 may further compare the characteristic of the magnetic signal for a selected voxel to characteristics of the magnetic signal in at least one other voxel in the subject's brain. This comparison provides indicates the relative strength of the signal in the selected voxel.

At block 220, the instructions 120 control the processor to determine a tissue characteristic of the voxel based on the comparison at block 216. The tissue characteristic may include a vessel type, a vessel orientation, a pathological condition, the like, or a combination thereof.

A vessel orientation may be identified based on the maximal amplitude with respect to the magnetic field. Vessels change their signal strength in a complex relationship when they are at different angles to the main magnetic field. Signal strength varies with orientation of vessel with respect to magnetic field. A low signal strength may indicate that orientation is not optimal. A 3D reconstruction of vascular images may be used to determine vessel orientation.

A vessel type includes an arterial vessel, a capillary, and a venous vessel. Voxels containing veins may be identified by their high amplitude, long phase lag, and lengthened period as compared with other voxels, and a high number of similar contiguous voxels. Voxels containing arteries may be identified by their high amplitude, short phase lag, a low number of similar contiguous voxels, a strong orientation signaling, and a period equal to the AIF. After identifying a vessel type for a plurality of voxels, the processor 126 may further controlled to assemble the plurality of magnetic signals into an angiogram or a venogram.

A pathological condition includes arterial stenosis, acute ischemia, chronic ischemia, Parkinson's Disease, Alzheimer's Disease, and aging.

The system 100 and method 100 will now be described by way of examples.

Figure 3:
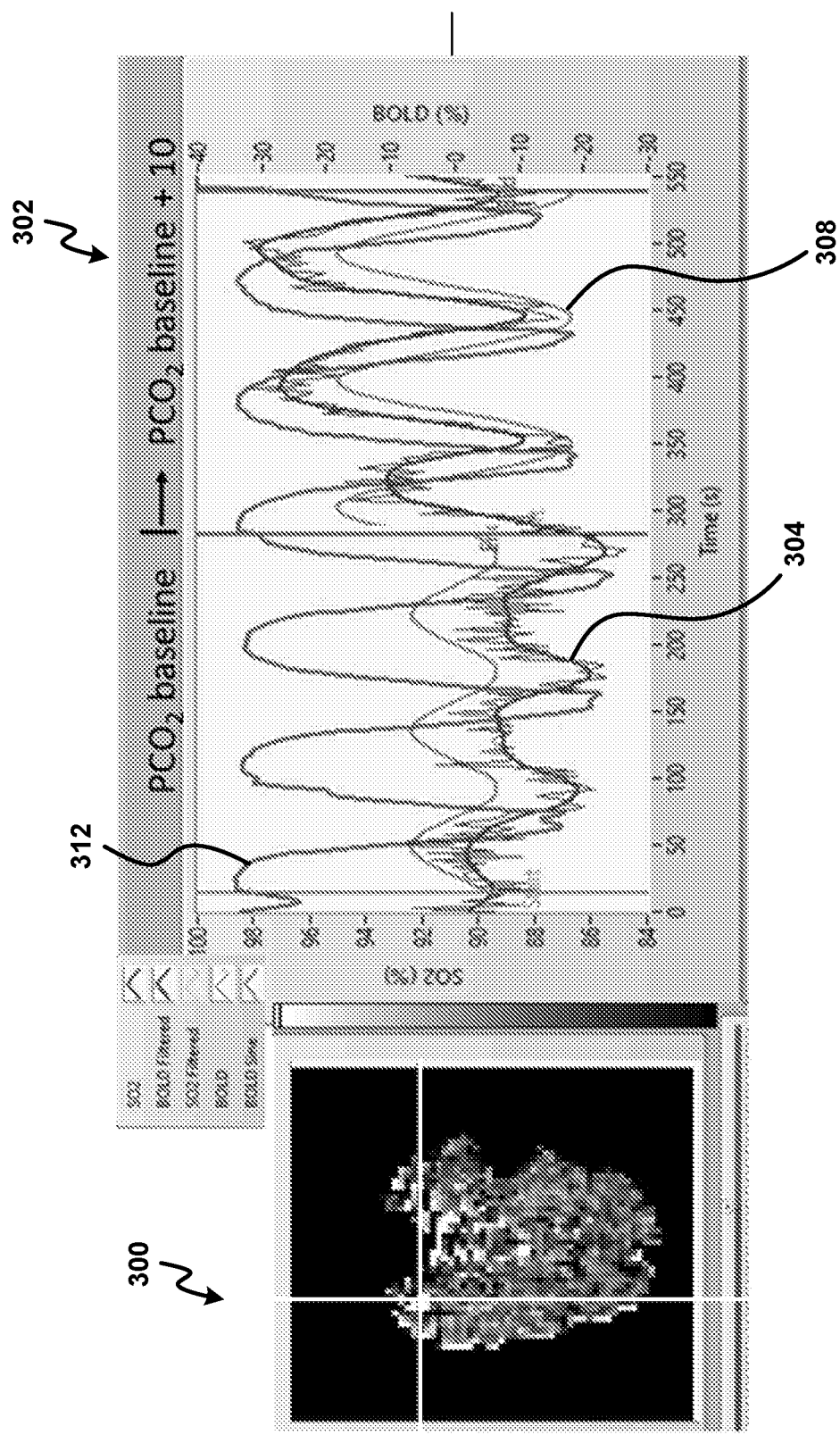
FIG. 3 is a graph showing exemplary performance of the method of FIG. 2.

FIG. 3 shows results obtained through exemplary performance of method 200. FIG. 3 includes a brain map 300 showing the selected voxel, indicated at the intersection of crosshairs. FIG. 3 further includes a graph 302 showing $SO_2$ on the left y-axis and BOLD signal (%) on the right y-axis. The BOLD signal for the selected voxel, as measured at block 208 of method 200, is shown at 304 and represents a zero-phase filtration. Curve 308 shows the dominant frequency of the BOLD signal, as determined by a Fourier transform during exemplary performance of block 212. In this example, the dominant frequency is 83 seconds at baseline and 89 seconds with hypercapnia (labeled as $PCO_2$ baseline+10). Oxygen saturation ($SO_2$) is shown at 312.

Figure 4A:
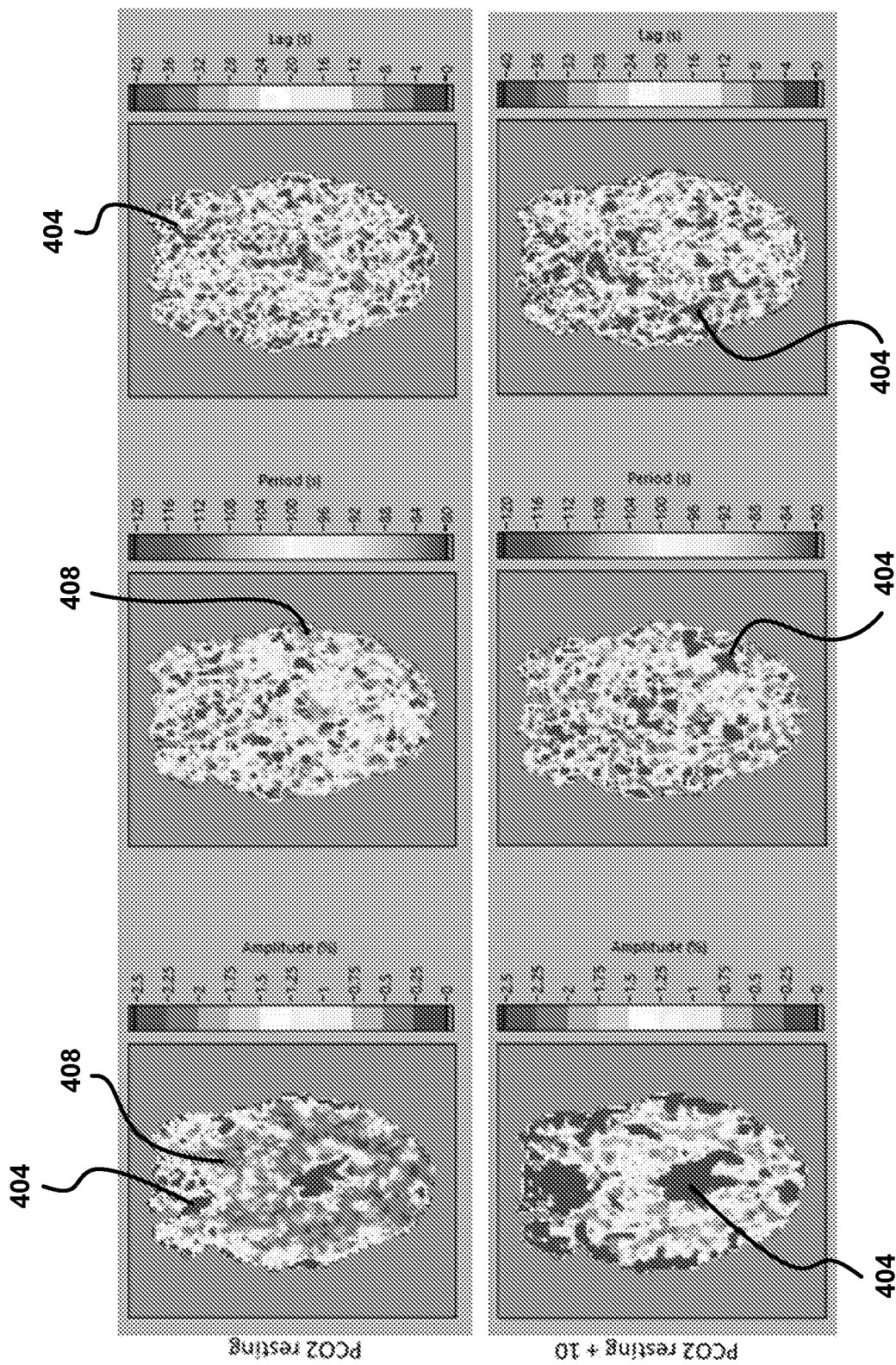
FIG. 4A is a brain map in color showing exemplary performance of the method of FIG. 2.
Figure 4B:
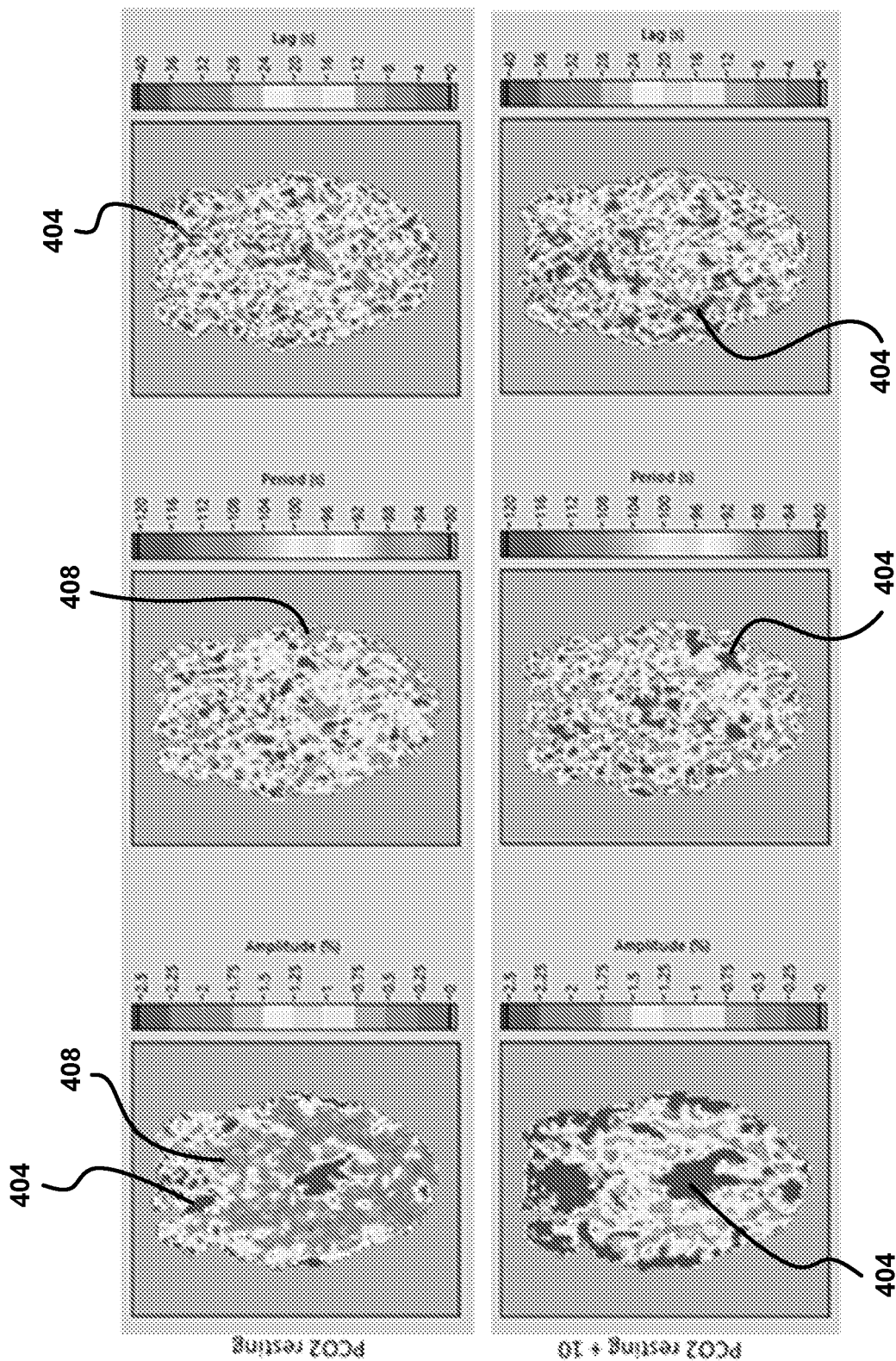
FIG. 4B is the brain map of FIG. 5A shown in grayscale.

FIGS. 4A and 4B show a brain map obtained through exemplary performance of method 200. The top row depicts results obtained when the normocapnia was maintained in the subject during performance of method 200. The bottom row depicts results obtained while maintaining a $PCO_2$ equal to baseline $PCO_2$ plus 10 mmHg. The first column illustrates amplitude (%), the second column indicates phase (seconds), and the third column illustrates lag (seconds). FIG. 4A is a colored brain map in which red 404 indicates the greatest relative values and blue 408 indicates the smallest relative values. FIG. 4B is a grayscale version of FIG. 4A.

FIGS. 4A and 4B demonstrate the effect of elevating $PCO_2$ in the subject during performance of method 200. As compared to the normocapnia results, the elevated $PCO_2$ results demonstrate increased amplitude throughout the subject's brain. Large increases in the amplitude of some voxels likely indicate that they contain venous blood vessels. As shown in the second column, the period is also greater in $PCO_2$+10 mmHg due to the increased volume of venous blood which was dispersed in tissues. The third column shows that phase lag in some voxels is also increased elevating $PCO_2$ which indicates that these voxels contain a greater tissue volume.

Figure 5:
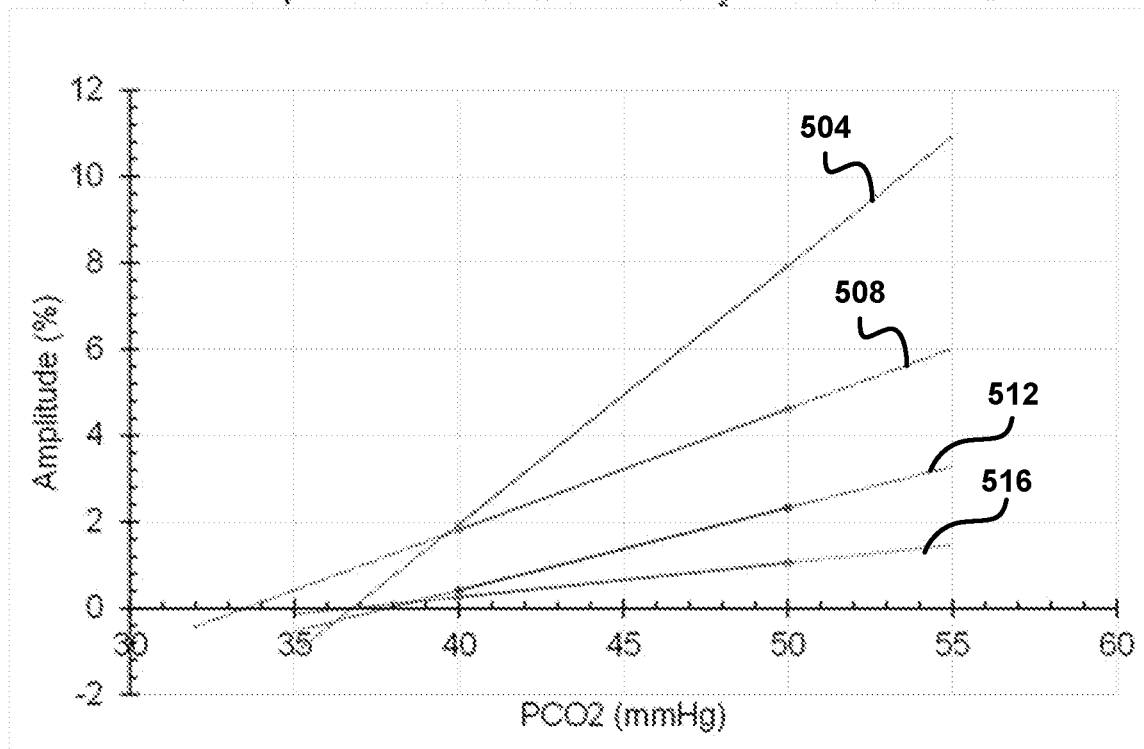
FIG. 5 is a graph showing the amplitude of a BOLD signal during exemplary performance of the method of FIG. 2.

FIG. 5 is a graph showing exemplary performance of method 200 and demonstrates the effect of $PCO_2$ on amplitude of the measured BOLD signal in four different voxels 504, 508, 512, 516. In FIG. 5, amplitude (%) of the BOLD signal is plotted on the y-axis and $PCO_2$ (mmHg) is plotted on the x-axis. Note in FIG. 3, that with the greater total flow (at higher $PCO_2$), as blood oxygen content increases, the oxygen delivery is a better match to the metabolic rate of oxygen ($CMRO_2$) resulting in higher BOLD signals. During hypoxic phase, arterial blood oxygen content is lower and the oxygen delivery raises little despite increased blood flow. The relationship between CBF and oxygen delivery is described in Equation 2:

$$CBF \times O_2 \text{ content} = \text{oxygen delivery} \qquad \text{Equation 2}$$

The present disclosure provides a number of advantages over the prior art of identifying pathologies using the DMN. Unlike the DMN which is characterized as a highly complex UFLM, the present disclosure provides that simple, induced periodic signals such as a sinusoidal signal can be implemented. It is possible to implement a periodic pattern with only one known frequency. Furthermore, the present method improves the accuracy of measurements. Since a sequential gas delivery system is used to control the amplitude of the signal, the signal-noise ratio can be optimized. Moreover, the present disclosure provides a method for identifying characteristics of vascular tissues based on their response to a periodic signal. In the brain, all arteries come directly from the lungs, through the heart and distribute over the arterial tree. As such all arteries will have the same frequency. As the blood passes through the capillaries of the voxels, it gets dispersed. Pathology such as enlarged cerebral blood volume, and mean transit times result in phase lag and elongation of the periodicity of the input pattern. The voxel-wise mapping of the changes in phase and period from the arterial input function helps characterize the vascular health of the underlying tissues. Phase and period changes can be compared to the AIF or compared over time or following an intervention. Additionally, the present disclosure describes the effect of $PCO_2$ in BOLD responses to a periodic signal and provides a method of modulating the $PCO_2$ in conjunction with a periodic [dOHb] to magnify changes and better identify vascular traits.

The present disclosure provides further advantages over a single bolus of a contrast agent. A single bolus has an uncontrolled profile because it depends on dispersion from the point of injection. In contrast, a sinusoid is predictably regular, independent of dispersion.

The many features and advantages of the invention are apparent from the detailed specification and, thus, it is intended by the appended claims to cover all such features and advantages of the invention that fall within the true spirit and scope of the invention. Further, since numerous modifications and changes will readily occur to those skilled in the art, it is not desired to limit the invention to the exact construction and operation illustrated and described, and accordingly all suitable modifications and equivalents may be resorted to, falling within the scope of the invention.

What is claimed is:

1. A method of implementing changes in deoxyhemoglobin concentration, the method comprising:
    targeting a sequence of partial pressures of oxygen in arterial blood ($P_aO_2$) values in a subject using a sequential gas delivery device in a periodic input pattern;
    measuring a blood-oxygen level dependent (BOLD) signal in a voxel of the subject's brain using a magnetic resonance imaging device while targeting the sequence of $P_aO_2$ values;
    comparing the periodic input pattern to the BOLD signal; and
    determining a tissue characteristic for the voxel based on the comparison.

2. The method of claim 1 wherein the BOLD signal comprises a periodic output pattern, the method further comprising computing a characteristic of the BOLD signal, wherein the characteristic of the BOLD signal comprises at least one of: an amplitude, a frequency, a period, and a phase lag.

3. The method of claim 2 wherein comparing the periodic input pattern to the BOLD signal comprises comparing the periodic input pattern to the characteristic of the BOLD signal.

4. The method of claim 1 further comprising measuring a BOLD signal over an artery and computing the arterial input function based on the BOLD signal over the artery.

5. The method of claim 4 further comprising comparing the periodic output pattern of the BOLD signal over the artery to the arterial input function.

6. The method of claim 5 further comprising:
    performing Fourier Transform on the BOLD signal over the artery to determine a dominant frequency; and
    comparing the dominant frequency to a dominant frequency of the arterial input function to determine a phase lag of the BOLD signal over the artery.

7. The method of claim 1 wherein the periodic input pattern of $P_aO_2$ values includes a peak value and a trough value, and wherein the difference between the peak value and the trough value is between 1% and 50%.

8. The method of claim 1 wherein the tissue characteristic is selected from a group consisting of: a vessel type, a vessel orientation, or a pathological condition.

9. The method of claim 1 further comprising
    varying the $P_aCO_2$ while targeting the sequence of $P_aO_2$ values in the periodic input pattern; and
    identifying a vascular characteristic for the voxel based on the comparison of the BOLD signal to the periodic input pattern.

10. The method of claim 9 wherein the vascular characteristic is one of: a change in voxel blood flow, relative cerebral blood flow (rCBF), or relative cerebral blood volume (rCBV) in comparison to other homologous parts of the brain, or in response to a vasoactive stimulus such as change in $PCO_2$.

11. The method of claim 9 wherein the varying comprises implementing a step change or a periodic change in $P_aCO_2$ between 15 mmHg and 90 mmHg.

12. The method of claim 9 further comprising targeting a first $P_aCO_2$ and a second $P_aCO_2$ in the subject's lung superimposed on a periodic input pattern of $PaO_2$.

* * * * *